United States Patent
Shadeck et al.

(10) Patent No.: US 8,414,606 B2
(45) Date of Patent: Apr. 9, 2013

(54) METHOD AND APPARATUS FOR REMOVING MATERIAL FROM AN INTERVERTEBRAL DISC SPACE AND PREPARING END PLATES

(75) Inventors: Louis M. Shadeck, Jacksonville, FL (US); Dana A. Oliver, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 46 days.

(21) Appl. No.: 13/013,384

(22) Filed: Jan. 25, 2011

(65) Prior Publication Data

US 2012/0101513 A1 Apr. 26, 2012

Related U.S. Application Data

(60) Provisional application No. 61/405,792, filed on Oct. 22, 2010.

(51) Int. Cl.
*A61B 17/32* (2006.01)
(52) U.S. Cl. .................................................. 606/170
(58) Field of Classification Search ............... 606/79–85, 606/167, 170, 171, 176, 177, 180
See application file for complete search history.

(56) References Cited

U.S. PATENT DOCUMENTS

| | | | |
|---|---|---|---|
| 4,573,448 A | 3/1986 | Kambin | |
| 5,286,253 A | 2/1994 | Fucci | |
| 5,313,962 A | 5/1994 | Obenchain | |
| 5,383,884 A | 1/1995 | Summers | |
| 5,540,708 A | 7/1996 | Lim et al. | |
| 5,911,701 A | 6/1999 | Miller et al. | |

(Continued)

FOREIGN PATENT DOCUMENTS

| | | |
|---|---|---|
| EP | 1698290 A1 | 9/2006 |
| GB | 2007098 A | 5/1979 |
| WO | 2005046492 A1 | 5/2005 |

OTHER PUBLICATIONS

PCT Search Report (PCT/US2006/060561) mailed Mar. 15, 2007 (7 pgs).

(Continued)

*Primary Examiner* — Ryan Severson
*Assistant Examiner* — Anh Dang
(74) *Attorney, Agent, or Firm* — Dicke, Billig & Czaja, PLLC

(57) ABSTRACT

Instrument and method for removing material from an intervertebral disc. The instrument includes outer and inner tubular members. The outer tubular member defines a passage and a cutting window. The inner tubular member is coaxially disposed within the passage, and defines a central lumen and a cutting tip. The cutting tip forms an open mouth having a plurality of teeth. Upon assembly, the cutting tip is exposed within the cutting window combining to define a shaving head. A manual decorticating implement is coupled to the outer tubular member and defining a scraping surface. A powered handpiece is coupled to the inner tubular member, and the shaving head is inserted into an intervertebral disc and positioned such that the cutting tip contacts targeted material (e.g., nucleus, annulus and/or end plate). The handpiece is activated to rotate the cutting tip relative to the cutting window. Contacted material is sheared between an edge of the cutting window and the teeth of the cutting tip. The manual decorticating implement is used to remove intervertebral disc material from an end plate.

15 Claims, 14 Drawing Sheets

U.S. PATENT DOCUMENTS

| | | | |
|---|---|---|---|
| 5,925,056 | A | 7/1999 | Thomas et al. |
| 5,980,504 | A | 11/1999 | Sharkey et al. |
| 6,030,401 | A | 2/2000 | Marino |
| 6,217,598 | B1 | 4/2001 | Berman et al. |
| 6,312,438 | B1 | 11/2001 | Adams |
| 6,440,138 | B1 | 8/2002 | Reiley et al. |
| RE38,018 | E | 3/2003 | Anctil et al. |
| 7,276,074 | B2 | 10/2007 | Adams et al. |
| 7,927,361 | B2 | 4/2011 | Oliver et al. |
| 2002/0038130 | A1 | 3/2002 | Adams |
| 2002/0138091 | A1 | 9/2002 | Pflueger |
| 2003/0191474 | A1 | 10/2003 | Cragg et al. |
| 2004/0127927 | A1 | 7/2004 | Adams |
| 2005/0065538 | A1 | 3/2005 | Van Wyk |
| 2005/0159767 | A1 | 7/2005 | Adams et al. |
| 2005/0209610 | A1 | 9/2005 | Carrison |
| 2006/0149268 | A1 | 7/2006 | Truckai et al. |
| 2006/0200153 | A1 | 9/2006 | Harp |
| 2007/0010822 | A1 | 1/2007 | Zalenski et al. |
| 2007/0149975 | A1* | 6/2007 | Oliver et al. .................... 606/79 |

OTHER PUBLICATIONS

PCT Search Report and Written Opinion mailed Feb. 20, 2012, 14 pgs.

* cited by examiner

METHOD AND APPARATUS FOR REMOVING MATERIAL FROM AN INTERVERTEBRAL DISC SPACE AND PREPARING END PLATES

CROSS-REFERENCE TO RELATED APPLICATION

This application claims priority under 35 U.S.C. §119(e) to U.S. Provisional Patent Application Ser. No. 61/405,792 filed on Oct. 22, 2010, and incorporated herein by reference.

BACKGROUND

The present disclosure relates to removal of intervertebral disc material. More particularly, it relates to a method and powered device for removing some or all of the material (tissue, cartilaginous bone, etc.) associated with an intervertebral disc, for example in performing a nucleotomy.

The vertebral spine includes, amongst other structures, a series of bony vertebrae, adjacent ones of which are supported and separated by an intervertebral disc. In a healthy spine, the discs maintain separation between the vertebrae, promoting fluid circulation throughout the spine, and providing a cushioning effect between the vertebral structures. An intervertebral disc generally includes an annulus fibrosis (or "annulus"), a nucleus pulposus (or "nucleus"), and opposing end plates. The end plates are akin to cartilaginous bone and serve to attach adjacent vertebrae to the disc. The nucleus is disposed between the end plates, circumferentially constrained by the annulus.

Intervertebral discs are elastic in nature, and can be damaged or displaced. For example, intervertebral discs can be overtly stressed by excessive movement, excess body weight, injury, disease, and/or gradual deterioration with age. Intervertebral disc injuries or other abnormalities can result in serious back pain and physical disability, and are often chronic and difficult to treat. For example, the annulus may bulge or tear, with the distended nucleus tissue compressing against a spinal nerve (e.g., disc herniation). Similarly, the disc may degenerate over time, leading to a collapse of the disc space.

Surgical procedures have been developed to repair damage or displaced intervertebral discs. These procedures include nucleotomies or discectomies in which a portion (e.g., the nucleus), or an entirety of the intervertebral disc is excised. Fusion is another accepted technique and entails the bony portions of the spine being fused together to limit the relative motion between adjacent vertebrae. Insertion/implantation of the fusion-inducing device(s) again requires removal of certain discal tissue. Similarly, disc decompression/fusion procedures require forming a hole in the annulus possibly followed by removal of nucleus tissue prior to backfilling with fusion material. More recently, nucleus replacement implants have been developed; these products also require removal of discal tissue (i.e., the nucleus and/or portions of, or all of, the annulus) prior to implantation. In several instances, preparation of cartilage adjacent the end plates is advantageous to foster bone growth and adhesion of fusion material.

Regardless of the exact procedure, various manual instruments for the removal of intervertebral disc material(s) are conventionally employed. These manual instruments include osteotomes, surgical chisels, guillotine cutting devices, etc. The highly confined nature of the surgical site associated with the intervertebral disc, the delicate surrounding structures (e.g., nerves), and the wide-range of material to be cut (i.e., the nucleus tissue is fairly soft, whereas the annulus tissue is quite tough), have likely given rise to the reliance upon simple, manual devices. While viable, use of manual instrumentation can render the procedure overly time consuming. Often times, several different manual instruments must be passed in and out of the surgical site multiple times in order to remove the desired discal material. This increases the chance of damage to sensitive structures adjacent to the spine (vascular and nervous). The manual instruments also require separate irrigation and suction device(s) to clean the surgical site during and after the procedure. Further, for certain procedures such as nucleotomies, manual surgical instruments require a surgeon to rely upon tactile feel to ensure that the annulus is not violated.

Injured and degenerated intervertebral discs pose serious health problems to a large number of patients. Many current and future treatments require the removal of nucleus and/or other discal tissue. Manual intervertebral disc material-removing tools are time-consuming to use, and require multiple other instruments. Available powered instruments for cutting intervertebral disc material do not afford the ability to effectively prepare end plates for fostering bone growth and adhesion of fusion material. As such, a surgeon removes the powered instrument from the intervertebral disc and inserts a manual instrument to prepare the end plates. Each time an instrument passes by nerves and arteries near the surgical site, there is an increased risk of injury thereto. Any advancement in the tools and related methods for performing this delicate material removal within or at the disc space will be well-received.

SUMMARY

Some aspects of the present invention relate to a method of removing material from an intervertebral disc otherwise defined by a nucleus surrounded by an annulus and opposing end plates. The method includes providing a surgical shaving instrument including an elongated outer tubular member and an elongated inner tubular member. The outer tubular member defines a central passage and a cutting window at a distal end thereof. The cutting window is defined by a perimeter edge and is fluidly connected to the central passage. The inner tubular member is coaxially disposed within the central passage, and further defines a central lumen and a cutting tip at a distal end thereof. The cutting tip forms a mouth that is open to the lumen and has a plurality of teeth formed along a perimeter. Upon final assembly, the cutting tip is exposed within the cutting window, with the cutting tip and cutting window combining to define a bodily material shaving head. A manual decorticating implement is coupled to the outer tubular member and defining a scraping surface. A powered handpiece is coupled to the inner tubular member such that the powered handpiece can cause the inner tubular member to rotate relative to the outer tubular member. The shaving head is inserted into an intervertebral disc and positioned such that the cutting tip contacts targeted material of the disc. The powered handpiece is activated to rotate the cutting tip relative to the cutting window. Contacted bodily material is, as a result, sheared between the edge of the cutting window and the teeth of the cutting tip. The manual decorticating implement is positioned such that the scraping surface contacts an end plate and intervertebral disc material is removed from the end plate using the scraping surface. Finally, the sheared and removed material is aspirated through the inner tubular member's lumen via the mouth. In one embodiment, the surgical instrument further includes an irrigation mechanism fluidly connected to the bodily material shaving head, with the method further including irrigating the material shaving head while shearing tissue.

Other aspects of the present invention relate to a surgical intervertebral disc material shaving instrument for use with a powered handpiece. The instrument includes outer and inner tubular members. The outer tubular member defines a central passage and a cutting widow. The cutting window is fluidly connected to the central passage and is defined by a perimeter edge having opposing, first and second longitudinal sides. At least four teeth are formed on each of the opposing longitudinal sides. The inner tubular member is coaxially disposed within the central passage, and defines a central lumen and a cutting tip. The cutting tip forms a plurality of circumferentially-extending teeth about a mouth that is otherwise fluidly connected to the lumen. Upon final assembly, the cutting tip is exposed within the cutting window, with the cutting window and the cutting tip combining to define a material shaving head adapted to shear intervertebral disc material, as well as to aspirate sheared material through the mouth and lumen.

DETAILED DESCRIPTION OF THE INVENTION

Figure 1:
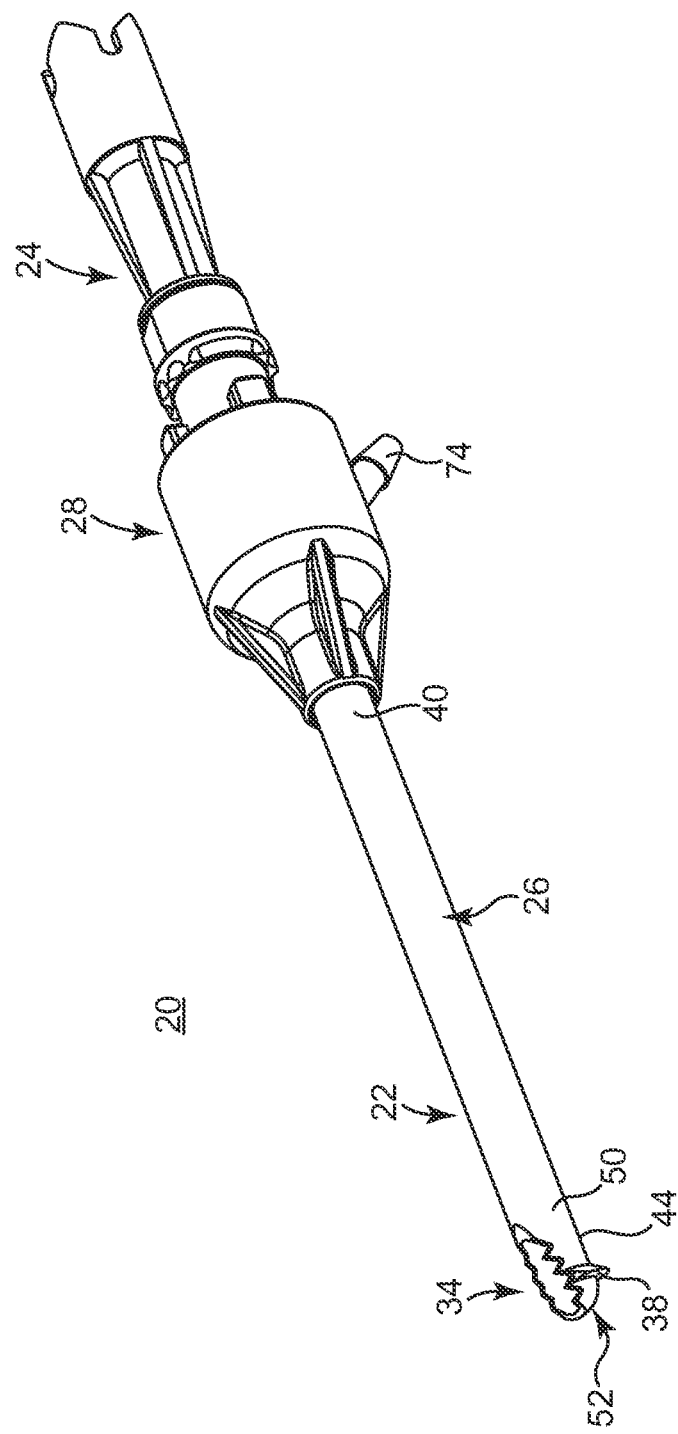
FIG. 1 is a perspective view of an intervertebral disc material shaving instrument in accordance with aspects of the present invention.
Figure 2:
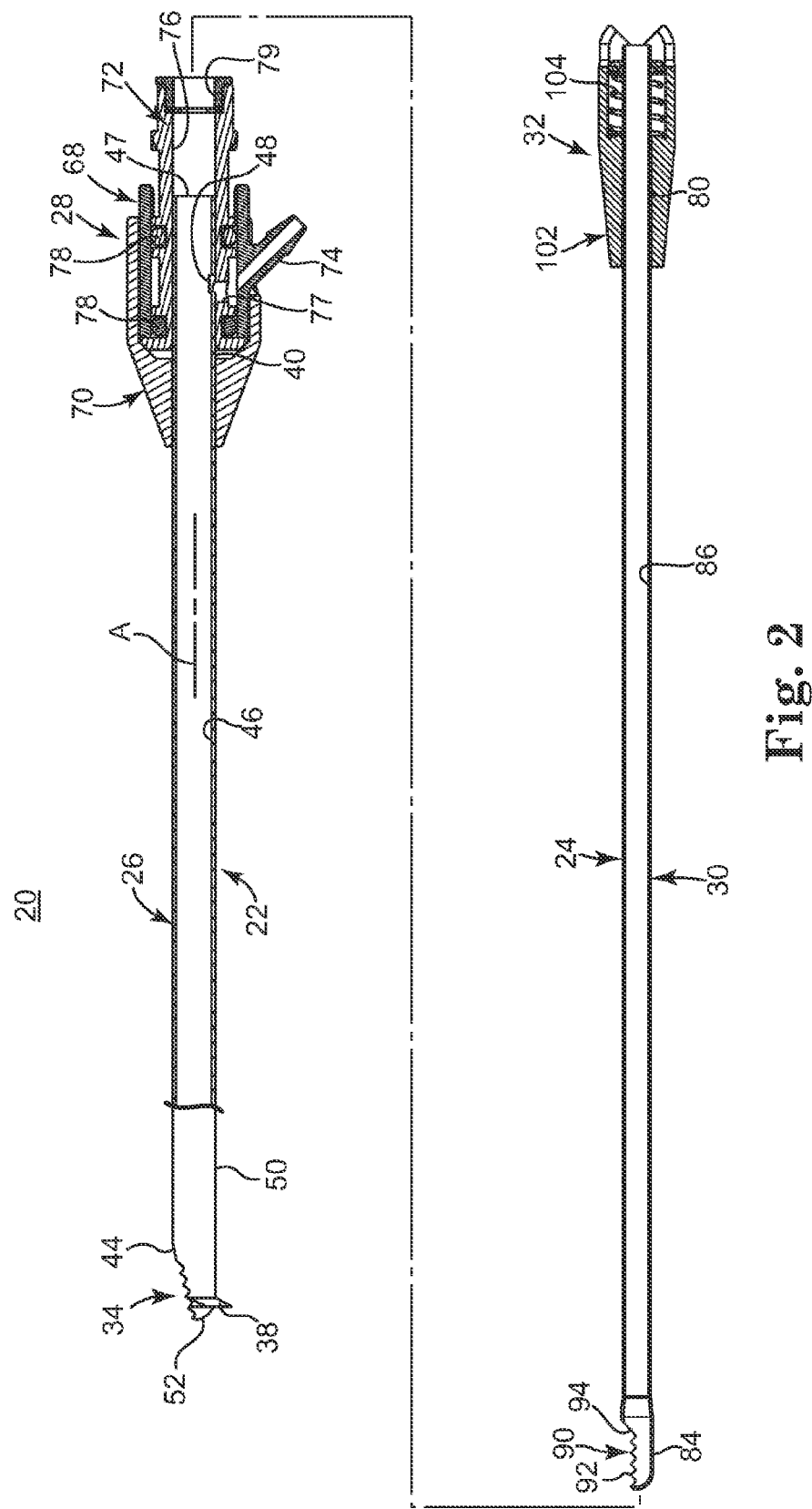
FIG. 2 is a cross-sectional, partial exploded view of the instrument of FIG. 1.

One embodiment of an intervertebral disc shaving instrument 20 in accordance with principles disclosed herein is shown in FIGS. 1 and 2. The instrument 20 includes an outer tubular assembly 22 and an inner tubular assembly 24. The outer tubular assembly 22 includes an outer tubular member 26 and a first hub assembly 28. Similarly, the inner tubular assembly 24 includes an inner tubular member 30 (best seen in FIG. 2) and a second hub assembly 32. Details on the various components are provided below. In general terms, however, the inner tubular member 30 is coaxially disposed within the outer tubular member 26, with the tubular members 26, 30 combining to define a bodily material shaving head 34 (FIG. 1). During use, the instrument 20 is coupled to a powered handpiece (not shown) that rotates the second hub assembly 32, and thus the inner tubular member 30, relative to the outer tubular member 26 in an oscillating fashion, to effectuate shearing of intervertebral disc material (not shown) at the shaving head 34. Additionally, a manual decorticating implement 38 is disposed on an outer surface of the outer tubular member 26. The implement 38 is useful to effectuate preparation of end plates (not shown).

The outer tubular member 26 is an elongated body defining a proximal segment 40 and a distal segment 44 maintaining the implement 38. Further, the outer tubular member 26 defines a central passage 46 (FIG. 2) extending from the distal segment 44 to the proximal segment 40. With specific reference to FIG. 2, the proximal segment 40 is adapted for connection to the first hub assembly 28, and defines a longitudinal axis A. For example, the proximal segment 40 forms a proximal open end 47 and a radial aperture 48 both of which are open to the central passage 46. As described below, the open end 47 facilitates placement of the inner tubular member 30 within the central passage 46, whereas the aperture 48 establishes fluid connection between the central passage 46 and a corresponding component of the first hub assembly 28. Alternatively, the proximal segment 40 can assume a variety of other forms.

In an alternative configuration, the outer tubular member 26 can define one or more bends in a region between the proximal segment 40 and the distal segment 44. For example, a bend region is disclosed in U.S. Patent Application Publication No. 2007/0149975 A1, the contents of which are hereby incorporated by reference in their entirety. In this embodiment, inner tubular member 30 conforms to the bend of outer tubular member 26.

The distal segment 44 terminates at a distal end 52 that is closed to the central passage 46 in one embodiment. Further, the distal segment 44 forms a cutting window 54 proximal the closed distal end 52. As described in greater detail below, the closed distal end 52 serves to distally shield a cutting surface of the inner tubular member 30, whereas the cutting window 54 exposes the surface. Thus, in one embodiment, an exterior surface of the closed distal end 52 is curved. The decorticating implement 38 defines a scraping surface provided on an exterior surface of the distal segment 44 and assists a surgeon in preparing end plates for fostering bone growth and adhesion of fusion material.

Figure 3A:
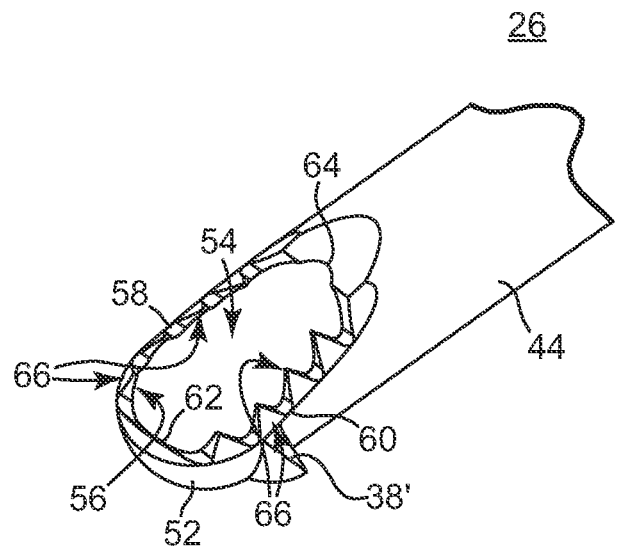
FIG. 3A is an enlarged top plan view of a distal segment of an outer tubular member portion of the instrument of FIG. 1.
Figure 3B:
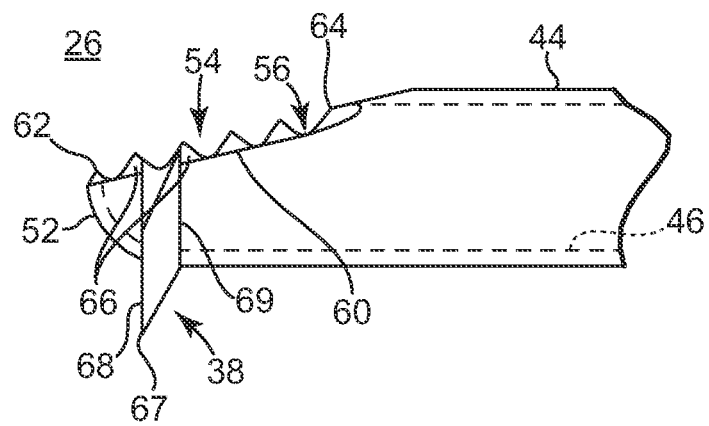
FIG. 3B is a side view of the segment of FIG. 3A.

With reference to FIGS. 3A and 3B, the cutting window 54 is open or fluidly connected to the central passage 46, and is defined by a perimeter edge 56. Relative to a longitudinal extension of the outer tubular member 26, the perimeter edge 56 generally defines opposing first and second longitudinal sides 58, 60, and opposing lateral ends 62, 64. With these spatial designations in mind, in one embodiment, the perimeter edge 56 forms a plurality of teeth 66 along each of the longitudinal sides 58, 60. The teeth 66 can assume a variety of forms, but in one embodiment are symmetrically arranged relative to the side 58, 60. In one embodiment, each of the sides 58, 60 includes or forms at least four teeth 66 to promote aggressive removal of intervertebral disc material. The teeth 66 are formed to be highly sharpened (e.g., tip width or thickness on the order of approximately 0.005 inch), and wrap or curve in conformance with a curvature of the remainder of the outer tubular member 26. In one embodiment, a tip-to-tip spacing between adjacent ones of the teeth 66 (along a corresponding side 58 or 60) is in the range of 0.04-0.06 inch, more preferably approximately 0.05 inch (±0.002 inch). Further, in one embodiment, the lateral ends 62, 64 are similarly sharp. While other dimensions and/or configurations can be employed, it has surprisingly been found that the above-described preferences are highly conducive to cutting the disparate material structures associated with an intervertebral disc.

Implement 38 extends from an outer surface of distal segment 44, defining an annular scraping surface 67 formed by a distal surface 68 and a proximal surface 69 of scraping implement 38. Distal surface 68 extends generally perpendicular from a circumference of outer tubular member 26, whereas proximal surface 69 is angled toward distal end 52. Implement 38, and thus distal surface 68 and/or proximal surface 69, can extend from the outer surface of distal segment 44 at various angles and at various positions with respect to distal segment 44. For example, implement 38 (including distal surface 68 and/or proximal surface 69) may extend at an oblique angle with respect to the outer surface of distal segment 44. Moreover, the implement 38 can extend directly from distal end 52, either at an oblique angle with respect thereto or parallel to a direction of extension of the distal segment 44. In any event, distal surface 68 and proximal surface 69 converge to form scraping surface 67, which is useful in removal of intervertebral disc material from end plates, as discussed below.

Returning to FIG. 2, the outer tubular member 26 is preferably formed of a hardened, surgically safe material, capable of supporting the inner tubular member 30 at high rotational/oscillation speeds (e.g., oscillation speed of 5,000 RPM). Thus, for example, the outer tubular member 26 is formed of 304 stainless steel; although a multitude of other materials are equally acceptable. Regardless, the central passage 46 is sized to coaxially receive the inner tubular member 30 in a manner allowing the inner tubular member 30 to rotate within the passage 46. In one embodiment, and as described below, a diameter of the central passage 46 is slightly greater than an outer diameter of the inner tubular member 30 to establish an irrigation pathway.

The first hub assembly 28 is adapted to receive and retain the proximal segment 40 of the outer tubular member 26, and in one embodiment includes an irrigation collar 68, an outer hub 70, and an inner hub 72. The irrigation collar 68 forms an irrigation port 74, and is configured to establish an irrigation fluid flow path to and from the central passage 46 of the outer tubular member 26 upon final assembly, as described below. The outer hub 70 and the inner hub 72 are adapted to secure the irrigation collar 68 to the outer tubular member 26, and thus can assume a variety of forms. In one embodiment, however, the outer hub 70 is sized for securement over the irrigation collar 68 as well as to the outer tubular member 26. Conversely, the inner hub 72 is sized for securement between the irrigation collar 68 and the outer tubular member 26, and in one embodiment forms a longitudinal passageway 76 and a radial opening 77. The longitudinal passageway 76 extends through an entirety of the inner hub 72, whereas the radial opening 77 is sized and positioned for fluid connection to the port 74 (and the radial aperture 48 of the outer tubular member 26) upon final assembly. To further promote a complete, sealed final relationship, the first hub assembly 28 further includes seals (e.g., O-rings) 78 and a seal hub 79 in one embodiment. Regardless, the first hub assembly 28 establishes a mechanism for delivering irrigation liquid from an irrigation source (not shown) to the shaving head 34 via the irrigation port 74 and the passage 46. The irrigation fluid serves to "clean" the surgical site, augment lubrication between the inner and outer tubular members 30, 26, and facilitate evacuation/aspiration of material from the surgical site (described below) by clearing "clogs" at the shaving head 34. Alternatively, the first hub assembly 28 can assume a variety of other forms.

The inner tubular member 30 is, similar to the outer tubular member 26, an elongated tube defining a proximal region 80 and a distal region 84. Further, the inner tubular member 30 defines a central lumen 86 extending from the proximal region 80 to the distal region 84. Once again, the inner tubular member 30 is sized to be coaxially received within the outer tubular member 26, with the proximal region 80 adapted for mounting to the second hub 32. The inner tubular member 30 has an overall construction capable of maintaining structural integrity when rotated at high speeds (e.g., oscillation speeds on the order of 5,000 RPM).

The distal region 84 forms a cutting tip 90. With additional reference to FIG. 3C, the cutting tip 90 includes a plurality of teeth 92 formed in a circumferentially-extending manner about a mouth 94. The teeth 92 are highly similar to the teeth 66 (FIGS. 3A and 3B) previously described, symmetrically arranged along opposite sides of the mouth 94 (it being understood that only one set of the teeth 92 are visible in FIG. 3C). Thus, in one embodiment, at least four of the teeth 92 are formed along each side of the mouth 94, and are highly sharpened. Further, in one embodiment, the teeth 92 are sized and positioned to be spatially aligned with the teeth 66 upon final assembly. Thus, in one embodiment, adjacent ones of the teeth 92 have a tip-to-tip spacing on the order of 0.04-0.06 inch, more preferably approximately 0.05 inch (±0.002 inch).

The mouth 94 is open to, and thus fluidly connected with, the lumen 86. As described in greater detail below, this configuration establishes an aspiration pathway from the mouth 94 and through the lumen 86. In this regard, material aspirated via the lumen 86/mouth 94 can be removed via an appropriate port associated with the second assembly hub 32. In one embodiment, the distal region 84 has a relatively large outer diameter, on the order of 3-8 mm, more preferably 4.5 mm, to reduce clogging of the lumen 86 during use. Alternatively, other dimensions can be employed.

Figure 3C:
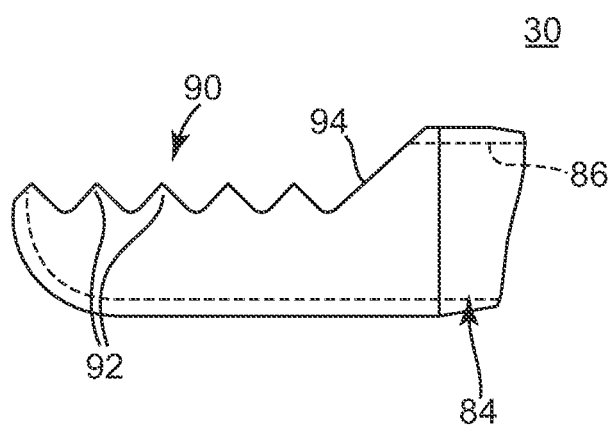
FIG. 3C is an enlarged, top plan view of a distal segment of an inner tubular member portion of the instrument of FIG. 1.
Figure 3D:
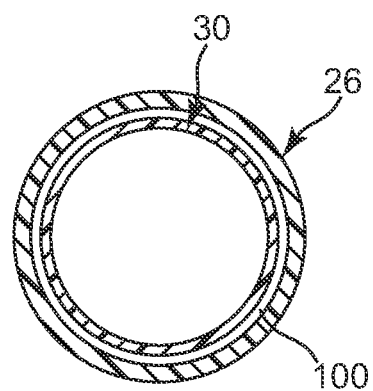
FIG. 3D is a cross-sectional view of the assembled instrument of FIG. 1.

Regardless of the exact configuration, at least as a majority of an inner diameter of the outer tubular member 26 is, in one embodiment, slightly larger than an outer diameter of the inner tubular member 30 so as to establish an annular gap 100 between the two components 26, 30 upon final assembly as shown in FIG. 3D. It will be understood that while FIG. 3D illustrates the inner tubular member 30 as being approximately centered relative to the outer tubular member 26, in actual practice, the inner tubular member 30 may contact the outer tubular member 26 at various radial locations. Along these lines, in one embodiment, the cutting tip 90 (FIG. 3C) of the inner tubular member 30 may have a diameter larger than a remainder thereof (such as by separately forming the cutting tip 90 and assembling to a remainder of the inner tubular member 30) that more closely matches an inner diameter of the outer tubular member 26. Regardless, a size of the gap 100 is exaggerated in the view of FIG. 3D for purposes of explanation. With additional reference to FIGS. 1 and 2, the annular gap 100 extends from the irrigation port 74 to the cutting window 54 to establish an interior irrigation pathway or mechanism by which an irrigation fluid can be delivered from the irrigation port 74 to the cutting window 54 (and thus the shaving head 34) via the annular gap 100. Alternatively, a separate irrigation tube (not shown) can be provided along (or formed with) an exterior of the outer tubular member 26.

With specific reference to FIG. 2, the second hub assembly 32 is sized for mounting to the inner tubular member 30 and includes, in one embodiment, a rotating hub 102 and a spring 104. The rotating hub 102 is adapted for coupling to a powered handpiece (not shown) as known in the art. The spring 104 facilitates releasable engagement with the powered handpiece, and in alternative embodiments, can be eliminated. To this end, the powered handpiece can assume a variety of forms, and can be electrically, or battery, or pneumatically powered.

Assembly of the instrument 20 includes securing the first hub assembly 28 to the outer tubular member 26. In one embodiment, the inner hub 72 is mounted over the proximal segment 40 such that the radial opening 77 is aligned, or otherwise fluidly connected to, the radial aperture 48. To ensure affixment of the inner hub 72 to the outer tubular member 26, an adhesive (e.g., Loctite adhesive) can be employed. The irrigation collar 68 is mounted over the inner hub 72 such that the port 74 is aligned with, or otherwise fluidly connected to, the radial opening 77 (and thus the radial aperture 48). The seals 78 are included at opposite sides of the port 74/radial opening 77 interface to provide a fluid-sealed relationship. The outer hub 70 is assembled or formed over the outer tubular member 26 and the irrigation collar 68. Where desired, an adhesive (e.g., Loctite adhesive) can be employed to bond the outer hub 70 to the irrigation collar 68.

The second hub assembly 32 is mounted to the proximal region 80 of the inner tubular member 30. An adhesive can be employed to bond the rotating hub 102 to the inner tubular member 30. The inner tubular member 30 is distally slid or inserted into and through the inner hub 72 and the outer tubular member 26 such that the cutting tip 90 is at or within the cutting window 54. To this end, the seal hub 79 sealingly engages an exterior of the inner tubular member 30 such that irrigation fluid within the outer tubular member 26 (e.g., within the gap 100 (FIG. 3D)) will not flow or leak proximal the seal hub 79.

Figure 4:
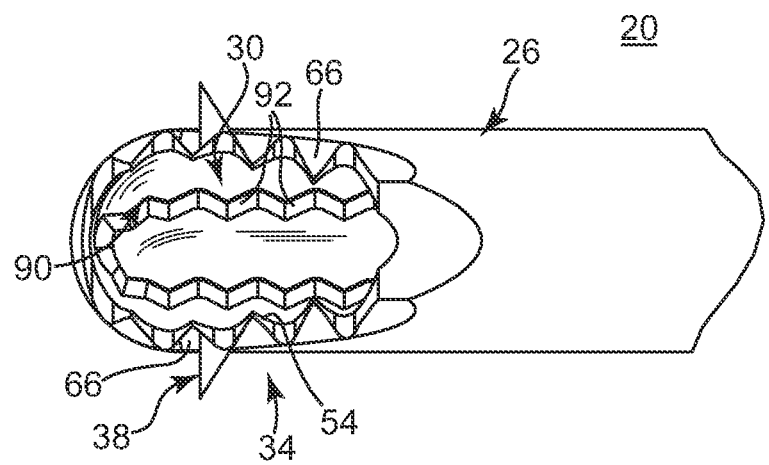
FIG. 4 is an enlarged, top plan view of the material shaving head formed by the instrument of FIG. 1

The shaving head 34 upon final assembly is shown in greater detail in FIG. 4. In particular, the cutting tip 90 is exposed at the cutting window 54. During use, as the inner tubular member 30 is rotatably oscillated relative to the outer tubular member 26, a shearing action is created between the teeth 92 of the cutting tip 90 and the teeth 66 of the cutting window 54. By providing a large number of sharp teeth, this shearing motion is able to aggressively remove material, yet provides a user with the ability to perform a controlled shaving or shearing operation, thus ensuring that only desired bodily material is contacted and cut. To this end, the closed distal end 52 of the outer tubular member 26 provides a blunt surface for non-traumatically contacting anatomical structures, thus providing instrument safety during "blind" cutting procedures. After removal of disc material, the scraping implement 38 is used in preparation of end plates by a surgeon. In particular, the implement 38 is brought into contact with an end plate and used to scrape material from the end plate by moving instrument 20 manually with respect to the end plate. In one particular embodiment, implement 38 can be scraped to cause bleeding of the end plate, which can provide an adequate surface for adhesion of material deposited thereon.

Figure 5:
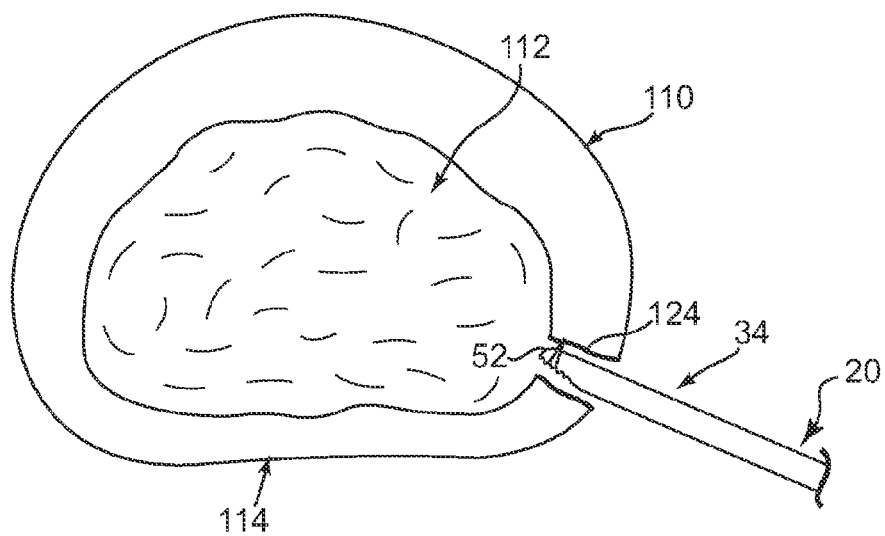
FIG. 5 is a simplified, top plan view of an intervertebral disc in combination with the instrument of FIG. 1 upon initial approach.
Figure 6:
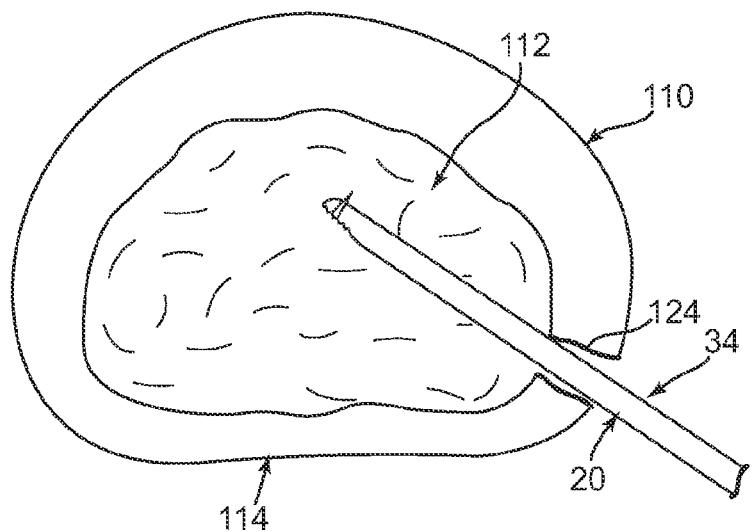
FIG. 6 is the view of FIG. 5 with the instrument fully inserted.
Figure 7:
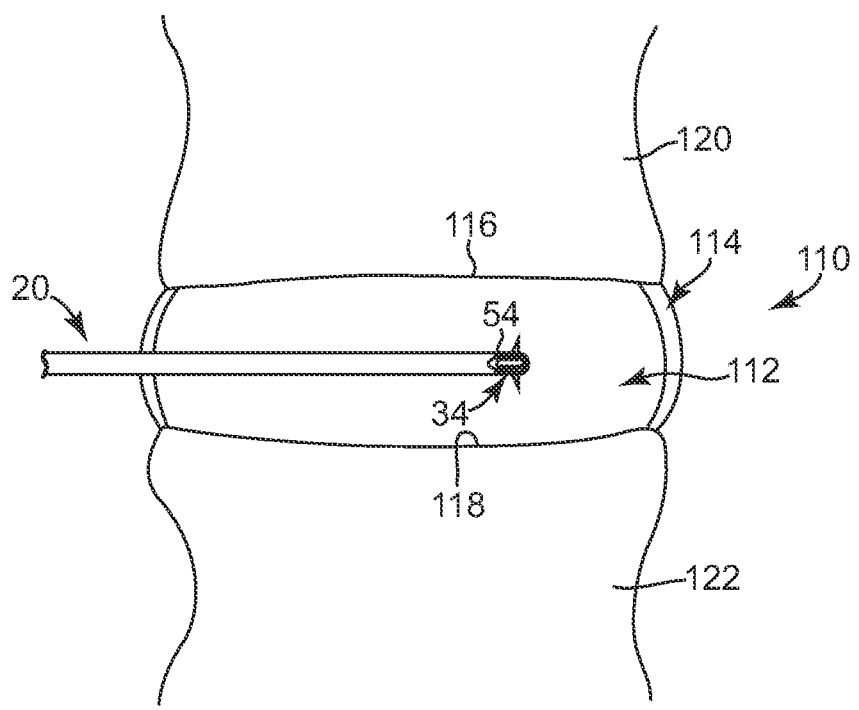
FIG. 7 is a simplified, side cross-sectional view of FIG. 6.
Figure 8:
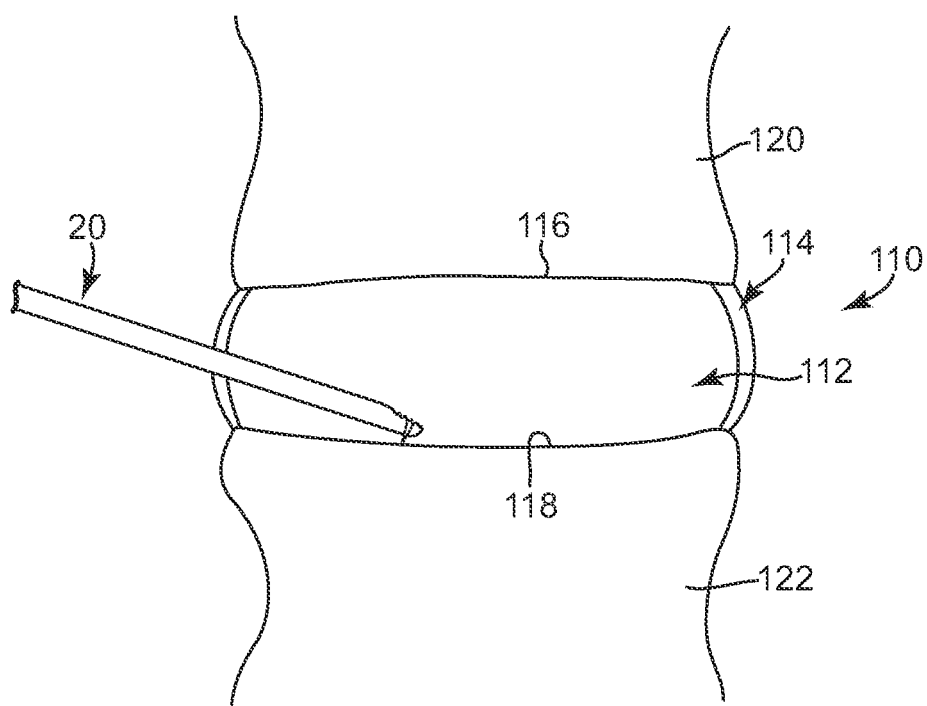
FIG. 8 is a side cross-sectional view with a scraping surface of a decorticating implement contacting an end plate.

One method of removing material from an intervertebral disc 110 using the intervertebral disc material shaving instrument 20 in accordance with principles disclosed herein is illustrated in FIGS. 5-8. By way of reference, the intervertebral disc 110 generally includes a nucleus 112 surrounded by an annulus 114 and opposing ends plates 116, 118 (FIGS. 7 and 8). The end plates 116, 118 in turn, are formed as part of adjacent vertebrae 120, 122 (FIGS. 7 and 8), respectively, and thus are akin to cartilaginous bone. With these general definitions in mind, the instrument 20 is employed to surgically remove or shave some or all of the material (e.g., tissue, cartilaginous bone, etc.) associated with the intervertebral disc 110. For example, one common procedure associated with treatment of a diseased intervertebral disc 110 is a nucleotomy in which a portion, or all, of the nucleus 112 is removed. With this in mind, the instrument 20 is deployed to the disc 110, for example via an posterior-lateral approach. Alternative approaches to the disc 110 are also acceptable and within the principles of the present disclosure, such as posterior approach, transforaminal approach, anterior approach, left or right lateral approach, etc. Regardless, as shown in FIG. 5, the shaving head 34 is positioned at an exterior of the annulus 114, aligned with an opening 124 formed therein. The opening 124 can be a naturally-occurring tear or similar passage; alternatively, the opening 124 can be surgically cut or otherwise created in the annulus 114. The closed distal end 52 contacts the annulus 114 in a non-traumatic manner, and protects the annulus 114 from potentially damaging, undesired contact with the teeth 66 (FIG. 3A) and 92 (FIG. 3C).

The shaving head 34 is then distally advanced within the annulus 114 and operated to remove some or all of the nucleus 112 region as shown in FIG. 6.

In particular, the instrument 20 is powered to effectuate removal of contacted material. More particularly, and with additional reference to FIG. 7, the powered handpiece (not shown) is activated, causing the cutting tip 90 (FIG. 3C) to rotationally oscillate relative to the cutting window 54. For example, the cutting tip 90 can be rotationally oscillated at speeds at or in excess of 5,000 RPM. In one embodiment, the powered handpiece is operated to rotate the inner tubular member 26 (FIG. 2) two revolutions in one direction, followed by two revolutions in the opposite direction, etc., although other operational formats are also acceptable. Nucleus tissue 112, otherwise in contact with the cutting tip 90/cutting window 54, is sheared between the two components, and aspirated from the surgical site via the mouth 94/lumen 86 (FIG. 2). Further, irrigation fluid is directly applied to the surgical site via the irrigation mechanism previously described so as to minimize clogging of the tissue shaving head 34, and in particular the mouth 94/lumen 86. The irrigation fluid can also serve to lubricate the surgical site as well as the inner tubular member 30/outer tubular member 26 interface.

After removal of nucleus tissue 112, other material of the intervertebral disc 110 can also be aggressively scraped and removed with the instrument 20. For example, the end plates 116, 118 can also be scraped as desired using scraping implement 38 without removing instrument 20 from disc 110. As illustrated in FIG. 8, scraping implement 38 can be positioned to scrape end plate 118. Instrument 20, and thus implement 38, can be scraped along end plate 118 in order to prepare the end plate 118 for bone growth and/or adhesion of fusion material. In particular, by scraping implement 38 across end plate 118, a top surface of the end plate 118 can be removed, encouraging blood to enter the end plate 118. During an autograft procedure, this blood promotes fusion between the end plate 118 and autograft material introduced in the disc 110. Tissue removed from end plate 118 due to scraping by implement 38 can be aspirated via the mouth 94/lumen 86 by further operation of the instrument 20. End plate 116 can be prepared in a similar manner.

Figure 9:
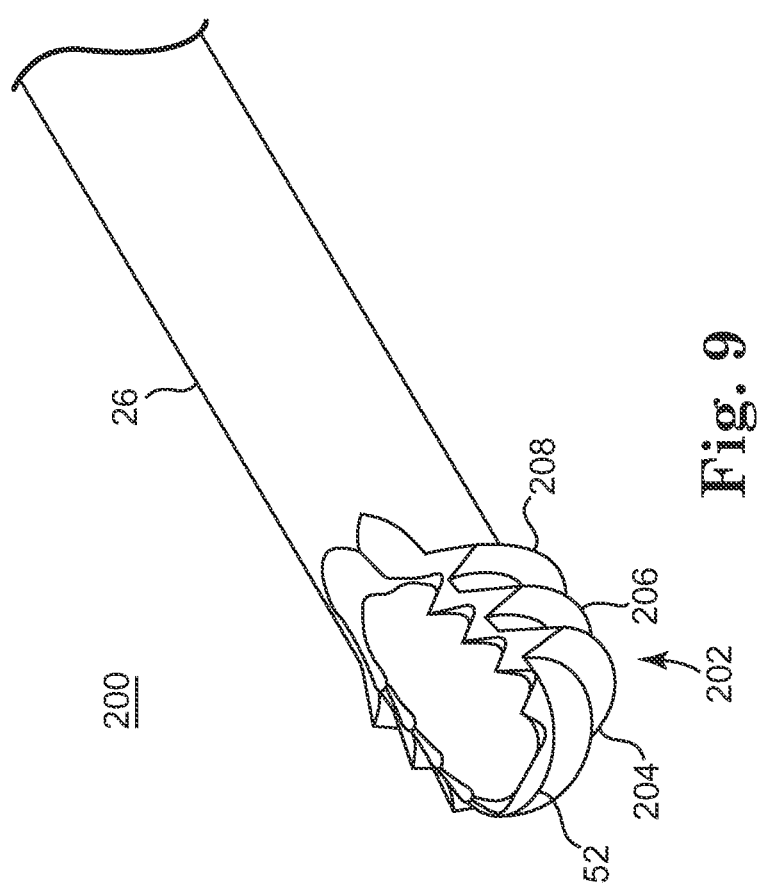
FIG. 9 is a perspective view of a distal segment of an outer tubular member portion of an alternative instrument.

Alternative decorticating implements to implement 38 can also be used. FIG. 9 illustrates an alternative distal end 200 having a manual scraping implement 202 including annular scraping surfaces 204, 206 and 208. The annular surfaces 204, 206 and 208 extend from an outer circumference of outer tubular member 26, and are similar in structure to annular surface 67 discussed above. Moreover, implement 202 is spaced apart from distal end 52 of outer tubular member 26. Each of the annular scraping surfaces 204, 206 and 208 are spaced apart from distal end 52 and arranged in parallel fashion to one another. In an alternative embodiment, implement 202 can include two annular scraping surfaces, wherein one of the surfaces 204, 206 and 208 is eliminated. In yet a further embodiment, the annular scraping surfaces 204, 206 and 208 are not parallel to one another, wherein one or more of the annular scraping surfaces are oblique to the outer surface. In one example, one of the annular scraping surfaces can form an acute angle with the outer tubular member, whereas another annular scraping surface forms an obtuse angle from a similar reference.

Figure 10:
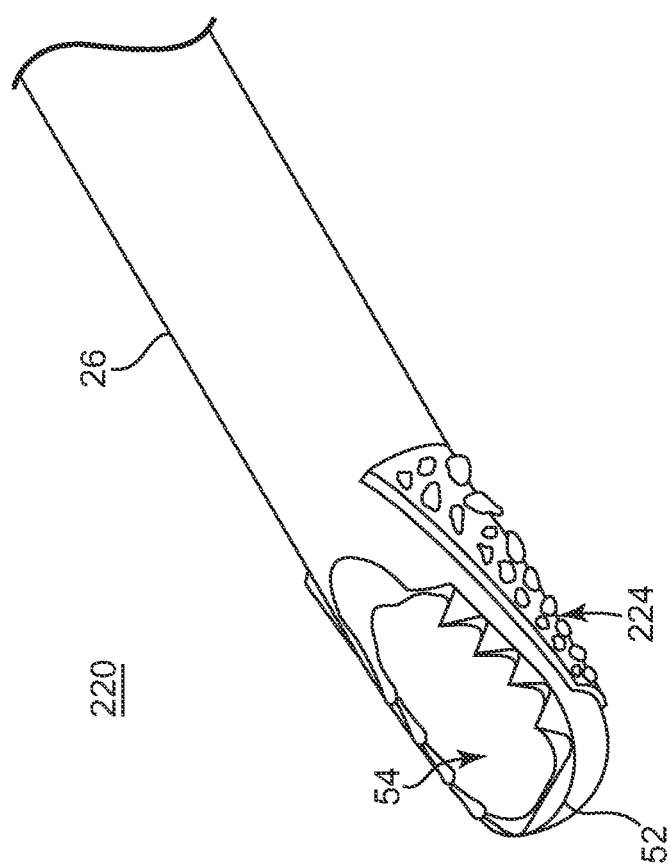
FIG. 10 is a perspective view of a distal segment of an outer tubular member portion of an alternative instrument.

FIG. 10 illustrates an alternative distal end 220 that includes scraping implement 224 positioned on an outer circumference of outer tubular member 26 on an opposite side of cutting window 54. Implement 224 includes a coating that forms a scraping surface to be used in preparation of end plates of an intervertebral disc. In one embodiment, the coating forms irregular protrusions extending from a circumference of the outer tubular member 26. The coating of implement 224, in one example, can be formed of a hard biocompatible material such as diamond, nickel coated tungsten and/or combinations thereof.

Figure 11:
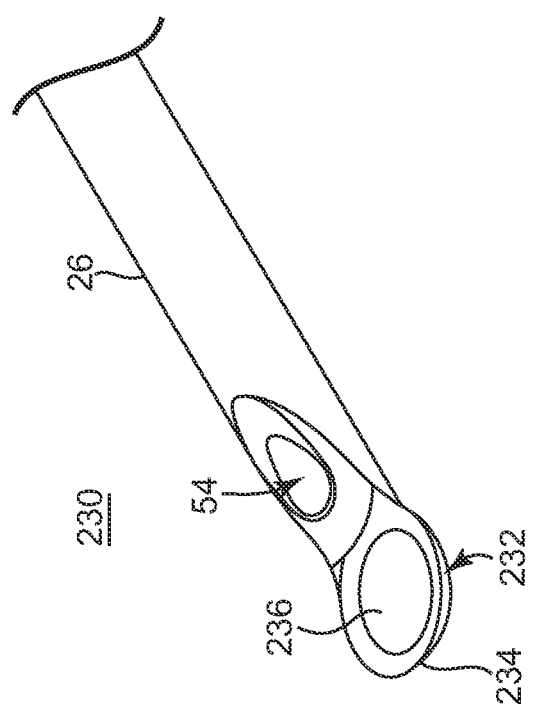
FIG. 11 is a perspective view of a distal segment of an outer tubular member portion of an alternative instrument.
Figure 12:
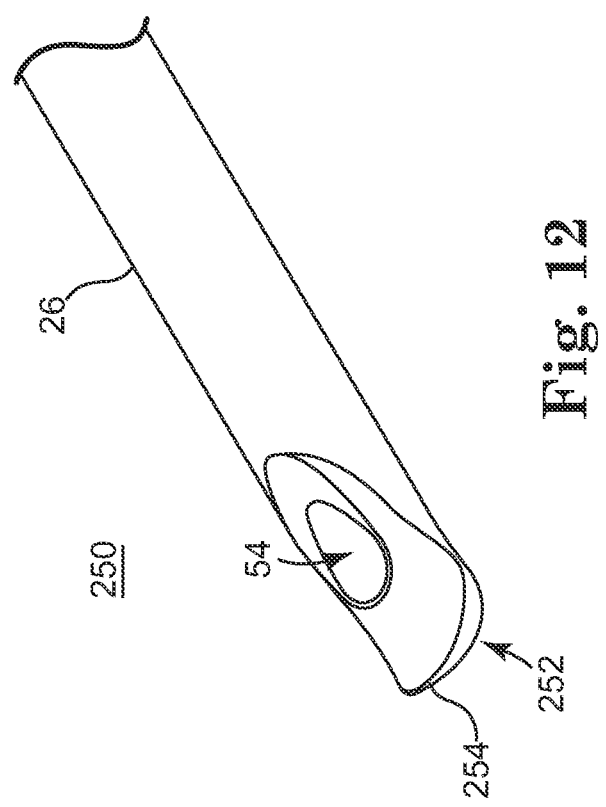
FIG. 12 is a perspective view of a distal segment of an outer tubular member portion of an alternative instrument.
Figure 13:
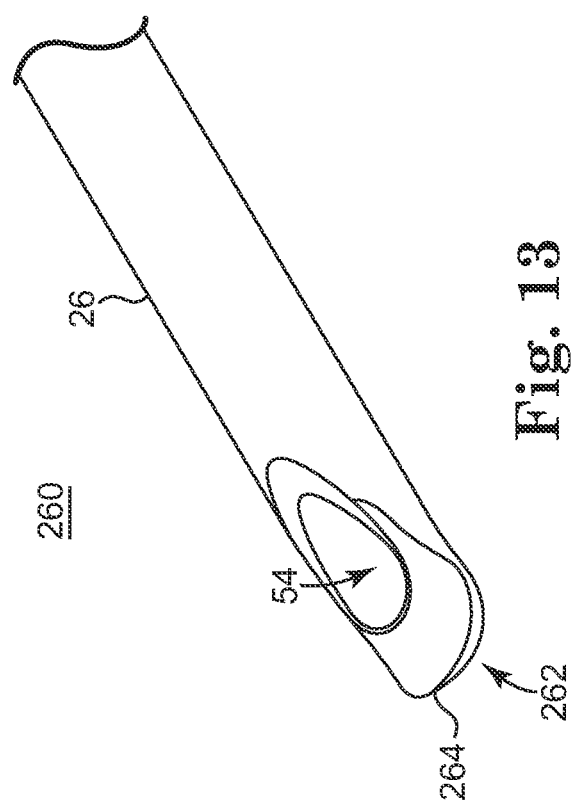
FIG. 13 is a perspective view of a distal segment of an outer tubular member portion of an alternative instrument.

In alternative embodiments, as illustrated in FIGS. 11-13, a manual scraping surface can extend distal a cutting window of the outer tubular member 26. FIG. 11 illustrates an alternative distal end 230 wherein a scraping surface 232 extends distal cutting window 54. The implement 232 defines an annular scraping surface 234 and an interior cup-like or ring-like feature 236 recessed from a top surface of the implement 232. During operation, a surgeon can rotate outer tubular member 26 such that scraping surface 234 can contact an endplate and remove material therefrom to prepare the endplate for bone growth and/or adhesion of fusion material.

FIG. 12 illustrates an alternative distal end 250 in which a manual decorticating implement 252 extends distal a cutting window 54 of outer tubular member 26. In particular, implement 252 includes an annular cutting surface 254 extending distal the cutting window 54.

FIG. 13 illustrates an alternative distal end 260 in which a manual decorticating implement 262 extends distal a cutting window 54 of outer tubular member 26. In particular, implement 262 includes an annular cutting surface 264 extending distal the cutting window 54.

Figure 14:
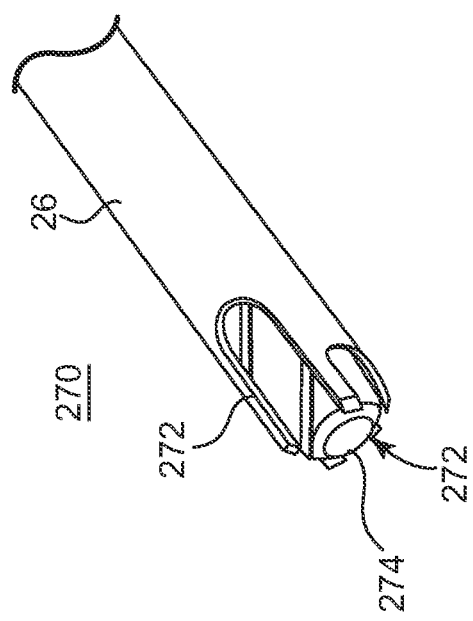
FIG. 14 is a perspective view of a distal segment of an outer tubular member portion of an alternative instrument.

FIG. 14 illustrates an alternative distal end 270 in which a manual decorticating implement 272 extends in a longitudinal direction to define a scraping surface. With distal end 270, a bur 274 is utilized to aid in removing intervertebral disc material.

Although the present invention has been described with reference to preferred embodiments, workers skilled in the art will recognize that changes can be made in form and detail without departing from the spirit and scope of the present invention.

What is claimed is:

1. A method for removing material of an intervertebral disc defined by a nucleus surrounded by an annulus and opposing end plates, the method comprising:
    providing a surgical shaving instrument including:
        an elongated outer tubular member defining a central passage and a cutting window at a distal segment thereof, the cutting window having a perimeter edge and being fluidly connected to the central passage, the perimeter edge defining a plurality of teeth;
        an inner tubular member coaxially disposed within the central passage, the inner tubular member defining a central lumen and a cutting tip at a distal region thereof, the cutting tip including a plurality of teeth formed about a mouth otherwise fluidly connected to the lumen,
        wherein upon final assembly, the cutting tip is exposed within the cutting window, and the cutting tip and cutting window combine to define a shaving head;
        a manual decorticating implement coupled to the outer tubular member and defining a scraping surface pointing in a direction opposite the plurality of teeth defined by the perimeter edge;
    coupling the inner tubular member to a powered handpiece adapted to cause the inner tubular member to rotate relative to the outer tubular member;
    inserting the shaving head into the intervertebral disc;
    positioning the shaving head such that the cutting tip contacts targeted material of the intervertebral disc;
    activating the powered handpiece to rotate the cutting tip relative to the cutting window;
    shearing the contacted intervertebral disc material between the perimeter edge of the cutting window and the teeth of the cutting tip;
    positioning the manual decorticating implement such that the scraping surface contacts an end plate;
    removing intervertebral disc material from the end plate using the scraping surface; and
    aspirating the sheared and removed intervertebral disc material through the lumen via the mouth.

2. The method of claim 1, wherein the implement includes a distal surface and a proximal surface extending from an outer circumference of the outer tubular member, the distal surface and proximal surface defining the scraping surface.

3. The method of claim 2, wherein the implement is spaced apart from a distal end of the outer tubular member.

4. The method of claim 2, wherein the distal surface is perpendicular to an axis of the outer tubular member.

5. The method of claim 4, wherein the proximal surface is oriented at an oblique angle with respect to the distal surface.

6. The method of claim 5, wherein the scraping surface is annular.

7. The method of claim 2, wherein the distal surface is oblique with respect to an axis of the outer tubular member.

8. The method of claim 1, wherein the implement includes a plurality of annular scraping surfaces extending from an outer circumference of the outer tubular member, the plurality of annular scraping surfaces spaced apart from one another along a length of the outer tubular member.

9. The method of claim 8, wherein the plurality of annular scraping surfaces includes three scraping surfaces.

10. The method of claim 8, wherein the plurality of annular scraping surfaces are parallel relative to one another.

11. The method of claim 8, wherein the plurality of annular scraping surfaces are non-parallel relative to one another.

12. The method of claim 1, wherein the perimeter edge of the cutting window defines at least eight teeth.

13. The method of claim 1, wherein the sheared material is nucleus tissue.

14. The method of claim 1, wherein the sheared material is annulus tissue.

15. The method of claim 1, wherein the removed material is cartilaginous end plate bone.

* * * * *